United States Patent
Schäfer et al.

[11] Patent Number: 5,968,874
[45] Date of Patent: Oct. 19, 1999

[54] SUBSTITUTED 2-PHENYLPYRIDINES USEFUL AS HERBICIDES

[75] Inventors: Peter Schäfer, Ottersheim; Gerhard Hamprecht, Weinheim; Elisabeth Heistracher, Mannheim; Olaf Menke, Altleiningen; Cyrill Zagar, Ludwigshafen; Michael Rack, Heidelberg; Norbert Götz, Worms; Albrecht Harreus, Ludwigshafen; Karl-Otto Westphalen, Speyer; Helmut Walter, Obrigheim; Ulf Misslitz, Neustadt, all of Germany

[73] Assignee: BASF Aktiengesellschaft, Ludwigshafen, Germany

[21] Appl. No.: 08/983,288

[22] PCT Filed: Jul. 23, 1996

[86] PCT No.: PCT/EP96/03243

§ 371 Date: Jan. 20, 1998

§ 102(e) Date: Jan. 20, 1998

[87] PCT Pub. No.: WO97/06143

PCT Pub. Date: Feb. 20, 1997

[30] Foreign Application Priority Data

Aug. 7, 1995 [DE] Germany .......................... 195 28 943

[51] Int. Cl.⁶ ..................... C07D 213/55; C07D 213/57; A01N 43/40
[52] U.S. Cl. ..................... 504/244; 546/330; 546/335
[58] Field of Search .................... 546/330, 335; 504/244

[56] References Cited

FOREIGN PATENT DOCUMENTS 43 23 916  1/1995  Germany .
195 00 758  7/1996  Germany .

*Primary Examiner*—Alan L. Rotman
*Attorney, Agent, or Firm*—Keil & Weinkauf

[57] ABSTRACT

Substituted 2-phenylpyridines I

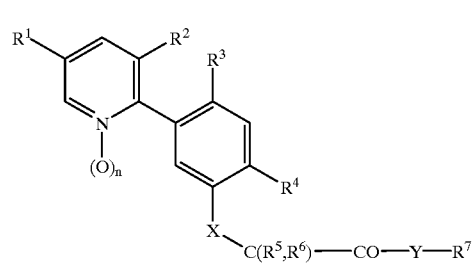

where n is 0, 1;

$R^1$ is halogen, $C_1$–$C_6$-haloalkyl;

$R^2$ and $R^3$ are H, halogen;

$R^4$ is cyano, halogen;

X and Y are —O—, —S—;

$R^5$ and $R^6$ are H, $C_1$–$C_4$-alkyl or together are a 1,2-ethylene, 1,3-propylene, 1,4-tetramethylene or 1,5-pentamethylene chain;

$R^7$ is $C_1$–$C_6$-haloalkyl, $C_3$–$C_6$-haloalkenyl, $C_2$–$C_6$-alkenyloxy-$C_1$–$C_4$-alkyl, $C_2$–$C_6$-alkenyloxy-$C_1$–$C_4$-alkoxy-$C_1$–$C_4$-alkyl, $C_3$–$C_6$-alkenyl, $C_3$–$C_6$-alkadienyl, $C_3$–$C_6$-alkynyl, $C_3$–$C_6$-cycloalkyl, $C_5$–$C_6$-cycloalkenyl, 3-oxetanyl, 3-thietanyl, phenyl, phenyl-$C_1$–$C_4$-alkyl or 5/6-membered heteroaryl having 1 to 3 hetero atoms selected from the group consisting of two oxygen atoms, two sulfur atoms and 3 nitrogen atoms, or $R^6$ and $R^7$ together are a 1,2-ethylene or 1,3-propylene chain which can have attached to it one or two $C_1$–$C_4$-alkyl substituents are used as herbicides and for the desiccation/defoliation of plants.

10 Claims, No Drawings

SUBSTITUTED 2-PHENYLPYRIDINES USEFUL AS HERBICIDES

The present invention relates to novel substituted 2-phenylpyridines of the formula I

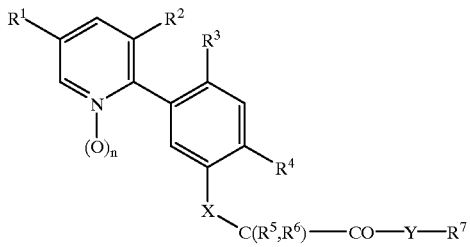

where the variables have the following meanings:
n is 0 or 1;
$R^1$ is halogen or $C_1$–$C_6$-haloalkyl;
$R^2$ and $R^3$ independently of one another are hydrogen or halogen;
$R^4$ is cyano or halogen;
X and Y independently of one another are oxygen or sulfur;
$R^5$ and $R^6$ independently of one another are hydrogen or $C_1$–$C_4$-alkyl or together are a 1,2-ethylene, 1,3-propylene, 1,4-tetramethylene or 1,5-pentamethylene chain;
$R^7$ is $C_1$–$C_6$-haloalkyl, $C_3$–$C_6$-haloalkenyl, $C_2$–$C_6$-alkenyloxy-$C_1$–$C_4$-alkyl, $C_2$–$C_6$-alkenyloxy-$C_1$–$C_4$-alkoxy-$C_1$–$C_4$-alkyl, $C_3$–$C_6$-alkenyl, $C_3$–$C_6$-alkadienyl, $C_3$–$C_6$-alkynyl, $C_3$–$C_6$-cycloalkyl, $C_3$–$C_6$-cycloalkenyl, 3-oxetanyl, 3-thietanyl, phenyl, phenyl-$C_1$–$C_4$-alkyl or 5- or 6-membered heteroaryl having one to three hetero atoms selected from the group consisting of two oxygen atoms, two sulfur atoms and 3 nitrogen atoms, it being possible for each phenyl ring and heteroaromatic ring to be unsubstituted or to have attached to it one to three substituents, in each case selected from the group consisting of halogen, nitro, cyano, $C_1$–$C_4$-alkyl, $C_1$–$C_4$-alkoxy and ($C_1$–$C_4$-alkoxy)carbonyl, or
$R^6$ and $R^7$ together are a 1,2-ethylene or 1,3-propylene chain which, if desired, can additionally have attached to it one or two $C_1$–$C_4$-alkyl substituents.

Moreover, the invention relates to the use of the compounds I as herbicides and/or for the desiccation and/or defoliation of plants, herbicidal compositions and compositions for the desiccation and/or defoliation of plants which comprise the compounds I as active ingredients, methods of controlling undesirable vegetation and for the desiccation and/or defoliation of plants by means of the compounds I, and processes for the preparation of the compounds I and of herbicidal compositions and compositions for the desiccation and/or defoliation of plants using the compounds I.

DE-A 43 23 916 and the corresponding WO 95/02580 disclose that certain 2-phenylpyridines have herbicidal and desiccant/defoliant properties. The compounds of those publications which are most similar structurally to the present compounds I have attached to them one of the following radicals instead of the group —C($R^5$,$R^6$)—CO—Y—$R^7$ when the substituents are chosen appropriately:

carboxyl-$C_1$–$C_6$-alkyl-, ($C_1$–$C_8$-alkoxy)carbonyl-$C_1$–$C_6$-alkyl-, ($C_1$–$C_8$-alkoxy)carbonyl-($C_3$–$C_7$-cycloalkyl)-, $C_1$–$C_4$-alkoxy-($C_1$–$C_4$-alkoxy)carbonyl-$C_1$–$C_6$-alkyl-, —$CH_2$—COO—($C_1$–$C_6$-alkylene)—COOH, —$CH_2$—COO—($C_1$–$C_6$-alkylene)—CO—($C_1$–$C_6$-alkoxy), —C($C_1$–$C_4$-alkyl)$_2$—COO—($C_1$–$C_6$-alkylene)—COOH, —C($C_1$–$C_4$-alkyl)$_2$—COO—($C_1$–$C_6$-alkylene)—CO—($C_1$–$C_6$-alkoxy), —CH($C_1$–$C_4$-alkyl)—COO—($C_1$–$C_6$-alkylene)—COOH or —CH($C_1$–$C_4$-alkyl)—COO—($C_1$–$C_6$-alkylene)—CO—($C_1$–$C_6$-alkoxy).

Other 2-phenylpyridines of the type of the compounds I which, however, have attached to them a tetrahydrofuranyloxy or succinyloxy radical instead of group —Y—$R^7$ are described in the earlier German Application DE-A . . . (P. 19 500 758.1).

However, the herbicidal action, of the known compounds, against the harmful plants is not always entirely satisfactory.

Accordingly, it was an object of the present invention to provide novel herbicidally active compounds which allow better specific control of undesirable plants than was possible to date. The object also extends to the provision of novel compounds with a desiccant/defoliant action.

We have found that this object is achieved by the substituted 2-phenylpyridines of the formula I defined at the outset. We have also found herbicidal compositions which comprise the compounds I and have a very good herbicidal action. We have furthermore found processes for the preparation of these compositions and methods of controlling undesirable vegetation by means of the compounds I.

Furthermore, we have found that the compounds I are also suitable for the defoliation and desiccation of parts of plants, suitable plants being crop plants such as cotton, potatoes, oilseed rape, sunflowers, soya beans or faba beans, in particular cotton. Accordingly, we have found compositions for the desiccation and/or defoliation of plants, processes for the preparation of these compositions and methods for the desiccation and/or defoliation of plants by means of the compounds I.

Depending on the substitution pattern, the compounds of the formula I may have one or more chiral centers, in which case they exist in the form of enantiomer or diastereomer mixtures. The invention relates to the pure enantiomers or diastereomers and also to mixtures of these.

The organic moieties mentioned in the definition of the substituents $R^1$ and $R^5$ to $R^7$ or as radicals on phenyl rings or heteroaromatic rings are, just like the meaning halogen, collective terms for individual enumerations of the individual group members. All carbon chains, i.e. all alkyl, haloalkyl, alkenyl, haloalkenyl and alkynyl moieties, can be straight-chain or branched. Halogenated substituents preferably have attached to them one to five identical or different halogen atoms. The meaning of halogen is in each case fluorine, chlorine, bromine or iodine.

Other exemplary meanings are given below:

$C_1$–$C_4$-alkyl and the alkyl moieties of $C_2$–$C_6$-alkenyloxy-$C_1$–$C_4$-alkyl, $C_2$–$C_6$-alkenyloxy-$C_1$–$C_4$-alkoxy-$C_1$–$C_4$-alkyl are: methyl, ethyl, n-propyl, 1-methylethyl, n-butyl, 1-methylpropyl, 2-methylpropyl and 1,1-dimethylethyl;

$C_1$–$C_6$-haloalkyl is: a $C_1$–$C_6$-alkyl radical, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1- dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, which is partially or fully substituted by fluorine, chlorine, bromine and/or iodine, i.e. chloromethyl, dichloromethyl, trichloromethyl, fluoromethyl, difluoromethyl, trifluormethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2, 2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl,3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy and the alkoxy moiety of $C_2$–$C_6$-alkenyloxy-$C_1$–$C_4$-alkoxy-$C_1$–$C_4$-alkyl are: methoxy, ethoxy, n-propoxy, 1-methylethoxy, n-butoxy, 1-methylpropoxy, 2-methylpropoxy and 1,1-dimethylethoxy;

($C_1$–$C_4$-alkoxy)carbonyl is: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl;

$C_3$–$C_6$-cycloalkyl is: cyclopropyl, cyclobutyl, cyclopentyl and cyclohexyl;

$C_5$–$C_6$-cycloalkenyl is: cyclopent-1-enyl, cyclopent-2-enyl, cyclopent-3-enyl, cyclohex-1-enyl, cyclohex-2-enyl and cyclohex-3-enyl;

$C_2$–$C_4$-alkenyl is: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl;

$C_3$–$C_6$-alkenyl is: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-2-en-1-yl, 1,2-dimethylbut-3-en-1-yl, 1,3-dimethylbut-2-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-3-en-1-yl, 3,3-dimethylbut-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

the alkenyl moieties of $C_2$–$C_6$-alkenyloxy-$C_1$–$C_4$-alkyl and $C_2$–$C_6$-alkenyloxy-$C_1$–$C_4$-alkoxy-$C_1$–$C_4$-alkyl are ethenyl or have one of the meanings mentioned for $C_3$–$C_6$-alkenyl;

$C_3$–$C_6$-alkadienyl is: propadienyl, 1,3-butadien-1-yl and 1,2-butadien-1-yl;

$C_3$–$C_6$-haloalkenyl is:. $C_3$–$C_6$-alkenyl as mentioned above which is partially or fully substituted by fluorine, chlorine, bromine and/or iodine, i.e. 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl;

$C_3$–$C_6$-alkynyl is: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

phenyl-$C_1$–$C_4$-alkyl is: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)-eth-1-yl and 1-(phenylmethyl)-prop-1-yl, preferably benzyl and 2-phenylethyl.

Examples of heteroaromatic rings $R^7$ are furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl, thienyl and pyrazolyl.

All phenyl and heterocyclic rings in the definition of $R^7$ are preferably unsubstituted or have attached to them a halogen, methyl, trifluoromethyl or methoxy substituent.

With a view to the use of the compounds of the formula I according to the invention as herbicides and/or as compounds with a defoliant/desiccant action, the variables preferably have the following meanings, in each case alone or in combination:

n is zero;

$R^1$ is halogen or $C_1$–$C_4$-haloalkyl, in particular trifluoromethyl;

$R^2$ is halogen, in particular chlorine;

$R^3$ is hydrogen or fluorine;

$R^4$ is cyano or chlorine;

X is oxygen;

Y is oxygen;

$R^5$ is hydrogen or methyl;

$R^6$ is hydrogen or methyl;

$R^7$ is $C_1$–$C_6$-haloalkyl, $C_3$–$C_6$-alkenyl, $C_3$–$C_6$-alkynyl, $C_3$–$C_6$-cycloalkyl, 3-oxetanyl or benzyl, or $R^6$ and $R^7$ together are a 1,2-ethylene or 1,3-propylene chain.

Particularly preferred are substituted 2-phenylpyridines of the formula Ia (= where n=0, $R^1$=trifluoromethyl, $R^2$ and $R^4$=chlorine, $R^3$=fluorine, X and Y=oxygen, $R^5$ hydrogen), in particular the compounds listed in Table 1:

TABLE 1

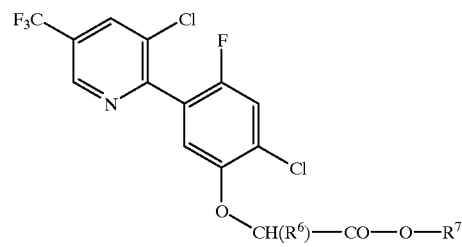

Ia

| No. | $R^6$ | $R^7$ | IR data ($\nu$[cm$^{-1}$]; $^1$H NMR data (in CDCl$_3$; Si(CH$_3$)$_4$ as the standard, $\delta$ [ppm]); m.p. [° C.]; |
|---|---|---|---|
| Ia.01 | H | —CH$_2$CH$_2$—O—CH=CH$_2$ | |
| Ia.02 | CH$_3$ | —CH$_2$CH$_2$—O—CH=CH$_2$ | |
| Ia.03 | H | —CH$_2$CH$_2$CH$_2$—O—CH=CH$_2$ | |
| Ia.04 | CH$_3$ | —CH$_2$CH$_2$CH$_2$—O—CH=CH$_2$ | |
| Ia.05 | H | —CH$_2$CH$_2$CH$_2$CH$_2$—O—CH=CH$_2$ | |
| Ia.06 | CH$_3$ | —CH$_2$CH$_2$CH$_2$CH$_2$—O—CH=CH$_2$ | |
| Ia.07 | H | —CH$_2$CH$_2$—O—CH$_2$CH$_2$—O—CH=CH$_2$ | |
| Ia.08 | CH$_3$ | —CH$_2$CH$_2$—O—CH$_2$CH$_2$—O—CH=CH$_2$ | |
| Ia.09 | H | —CH$_2$—CH=CH$_2$ | |
| Ia.10 | CH$_3$ | —CH$_2$—CH=CH$_2$ | see Preparation Example 1 |
| Ia.11 | H | —CH$_2$—CH=CH—CH$_3$ | |
| Ia.12 | CH$_3$ | —CH$_2$—CH=CH—CH$_3$ | |
| Ia.13 | H | —CH$_2$—C(CH$_3$)=CH$_2$ | |
| Ia.14 | CH$_3$ | —CH$_2$—C(CH$_3$)=CH$_2$ | |
| Ia.15 | H | —CH(CH$_3$)—CH=CH$_2$ | |
| Ia.16 | CH$_3$ | —CH(CH$_3$)—CH=CH$_2$ | |
| Ia.17 | H | —C(CH$_3$)$_2$—CH=CH$_2$ | |
| Ia.18 | CH$_3$ | —C(CH$_3$)$_2$—CH=CH$_2$ | |
| Ia.19 | H | —CH$_2$—C≡CH | see Preparation Example 2 |
| Ia.20 | CH$_3$ | —CH$_2$—C≡CH | |
| Ia.21 | H | —CH$_2$—C≡C—CH$_3$ | |
| Ia.22 | CH$_3$ | —CH$_2$—C≡C—CH$_3$ | |
| Ia.23 | H | —CH(CH$_3$)—C≡CH | |
| Ia.24 | CH$_3$ | —CH(CH$_3$)—C≡CH | |
| Ia.25 | H | —C(CH$_3$)$_2$—C≡CH | |
| Ia.26 | CH$_3$ | —C(CH$_3$)$_2$—C≡CH | |
| Ia.27 | H | cyclopentyl | |
| Ia.28 | CH$_3$ | cyclopentyl | |
| Ia.29 | H | cyclohexyl | |
| Ia.30 | CH$_3$ | cyclohexyl | |
| Ia.31 | H | 3-oxetanyl | |
| Ia.32 | CH$_3$ | 3-oxetanyl | see Preparation Example 3 |
| Ia.33 | —CH$_2$—CH$_2$— | | see Preparation Example 4 |
| Ia.34 | —CH$_2$—CH(CH$_3$)— | | see Preparation Example 5 |
| Ia.35 | —CH(CH$_3$)—CH$_2$— | | |
| Ia.36 | —CH$_2$—CH$_2$—CH$_2$— | | |
| Ia.37 | —CH(CH$_3$)—CH$_2$—CH$_2$— | | |
| Ia.38 | —CH$_2$—CH(CH$_3$)—CH$_2$— | | |
| Ia.39 | —CH$_2$—CH$_2$—CH(CH$_3$)— | | |
| Ia.40 | H | —CH$_2$—CCl$_3$ | |
| Ia.41 | CH$_3$ | —CH$_2$—CCl$_3$ | |
| Ia.42 | H | —CH$_2$—CF$_3$ | |

TABLE 1-continued

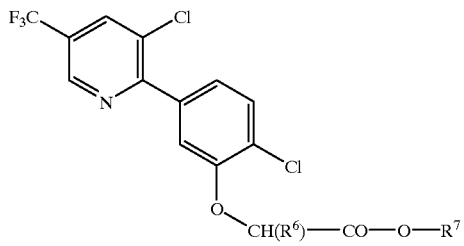

Ia

| No. | R⁶ | R⁷ | IR data (ν[cm⁻¹]; ¹H NMR data (in CDCl₃; Si(CH₃)₄ as the standard, δ [ppm]); m.p. [° C.]; |
|---|---|---|---|
| Ia.43 | CH₃ | —CH₂—CF₃ | see Preparation Example 6 |
| Ia.44 | H | —CH₂-phenyl | |
| Ia.45 | CH₃ | —CH₂-phenyl | |

Furthermore, the following substituted 2-phenylpyridines of the formulae Ib to Id are particularly preferred, in particular the compounds Ib.01–Ib.45, which differ from the corresponding compounds Ia.01–Ia.45 only by the fact that $R^3$ is hydrogen:

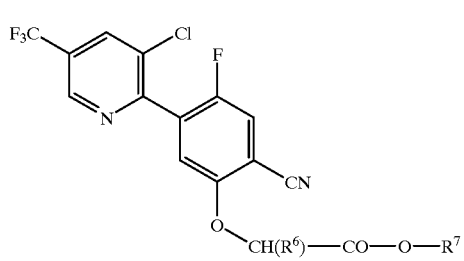

Ib the compounds Ic.01–Ic.45, which differ from the corresponding compounds Ia.01–Ia.45 only by the fact that $R^4$ is cyano:

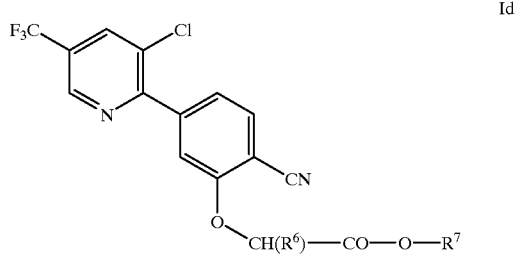

Ic the compounds Id.01–Id.45, which differ from the corresponding compounds Ia.01–Ia.45 only by the fact that $R^3$ is hydrogen and $R^4$ is cyano:

Id

The substituted 2-phenylpyridines of the formula I can be obtained in various ways, for example by one of the following processes:

Process A)

Reaction of acid chlorides II with alcohols or thiols HY—R⁷ in the presence of a base (cf., for example, H. Henecka in Houben-Weyl, Methoden der Organischen Chemie [Methods in Organic Chemistry], Vol. VIII, 4th Edition, Stuttgart 1952, pages 543 et seq. and A. Schöberl and A. Wagner in Houben-Weyl, Methoden der Organischen Chemie [Methods in Organic Chemistry], Vol. IX, 4th Edition, Stuttgart 1955, pages 754 et seq.):

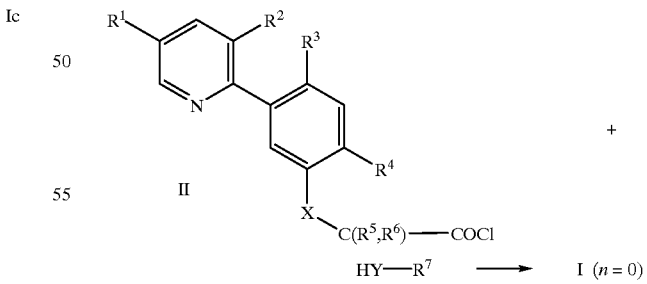

The alcohols/thiols HY—R⁷ can also be employed in the form of their salts, in particular the sodium and potassium salts, in which case the presence of a base is not necessary.

The process is conventionally carried out in an inert solvent or diluent, in particular in a halogenated hydrocarbon, such as dichloromethane, chloroform, 1,2-dichloroethane and carbon tetrachloride.

Suitable bases are, for example, alkali metal (hydrogen) carbonates, such as sodium carbonate and sodium hydrogen carbonate, furthermore nitrogen bases, such as pyridine, 4-dimethylaminopyridine and triethylamine.

The reaction temperature is normally at from 0 to 100° C.

The reactants are conventionally employed in approximately stoichiometric amounts, but an excess of one of the reactants may be advantageous, for example with a view to as complete as possible a reaction of the other reactant.

The acid chlorides of the formula II have already been described in the earlier application DE-A . . . (P. 19 500 758.1). They are expediently prepared by chlorinating the corresponding free carboxylic acids or their alkali metal salts.

The chlorination can be effected either in the absence of a solvent in an excess of the halogenating agent or in an inert solvent or diluent, in particular in an aprotic solvent, for example in diethyl ether, benzene or in carbon disulfide.

Suitable chlorinating agents are, for example, thionyl chloride, oxalyl chloride, phosphorus trichloride, phosphorus pentachloride, phosphorus oxychloride, phosgene, diphosgene or triphosgene.

More information for carrying out such chlorination reactions can be found in the following references, which are referred to by way of example:

A. J. Meyers and M. E. Flanagan, Org. Synth. 71, 107 (1992);

H. J. Scheifele Jr. and D. F. DeTar, Org. Synth. Coll. Vol. IV, page 34 (1963);

G. H. Coleman et al., Org. Synth. Coll. Vol. III, page 712 (1955);

H. Henecka in Houben-Weyl, Methoden der Organischen Chemie [Methods in Organic Chemistry], Vol. VIII, 4th Edition, Stuttgart 1952, page 463 et seq.

Those carboxylic acids corresponding to the acid chlorides II which are not known from, for example, DE-A 43 23 916 can be obtained as described in this publication.

Process B)

3-Pyridylphenols or 3-pyridylthiophenols of the formula III are reacted with alkylating agents of the formula IV in the presence of a base:

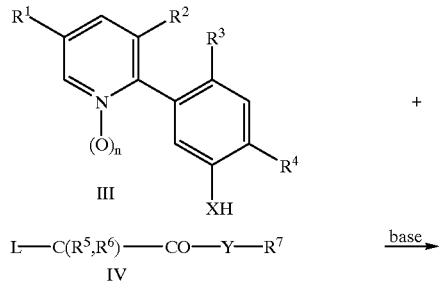

L is chlorine, bromine, iodine, methylsulfonyloxy, trifluoromethylsulfonyloxy, phenylsulfonyloxy or p-toluenesulfonyloxy.

As a rule, the process is carried out in an inert solvent or diluent which is preferably aprotic, i.e. in N,N-dimethylformamide, dimethyl sulfoxide, acetone, N-methylpyrrolidone, acetonitrile, or in an ether, such as diethyl ether, tetrahydrofuran and 1,4-dioxane.

Examples of suitable bases are alkali metal carbonates and alkali metal hydrogen carbonates, such as sodium hydrogen carbonate, potassium hydrogen carbonate, sodium carbonate and potassium carbonate, alkali metal alcoholates, such as sodium methanolate and potassium tert-butanolate, alkali metal hydroxides, such as sodium hydroxide, and alkali metal hydrides, such as sodium hydride.

More information for carrying out such alkylation reactions can be found, for example, in the following references:

re alkylation of phenols using α-carbonylsulfonates:
U. Burkard and F. Effenberger, Chem. Ber. 119, 1594 (1986);
J. Bierdermann et al., J. Med. Chem. 29, 1183 (1986);
R. B. Rogers et al., U.S. Pat. No. 4,725,683;

re alkylation of phenols using α-haloesters:
R. Aneja et al., Tetrahedron 2, 203 (1958);
EP-A 380 043;
C. R. Edwards et al., J. Heterocycl. Chem. 24, 495 (1987);
C. P. Phadke et al., Synthesis 5, 413 (1986);
K. G. Watson, U.S. Pat. No. 4,837,355;
V. Elango et al., U.S. Pat. No. 4,908,476;
G. Schlegel et al., U.S. Pat. No. 4,978,774;
U. Burkard and F. Effenberger, Chem. Ber. 119, 1594 (1986);
H. Sugihara et al., Chem. And Pharm. Bull. 35, 1919 (1987);
S. Fujinawa et al., U.S. Pat. No. 4,625,053;

re alkylation of thiophenols using α-carbonylsulfonates:
U. Burkard and F. Effenberger, Chem. Ber. 119, 1594 (1986);

re alkylation of thiophenols using α-haloesters:
M. B. Floyd, U.S. Pat. No. 4,983,753;
E. Campaigne and A. R. McLaughlin, J. Heterocycl. Chem. 20, 623 (1983);
J. Durman et al., J. Chem. Soc. Perkin Trans., 1939 (1986);
M. Kawada et al., Chem. Pharm. Bull. 34, 1939 (1986);
H. Sugihara et al., Chem. And Pharm. Bull. 35, 1919 (1987).

The phenols and thiophenols III have already been disclosed in DE-A 43 23 916.

The alkylating agents IV which are not already known, for example from

S. F. Karaev et al., Azerb. Khim. Zh. 4, 30–33 (1974) {see also Chemical Abstracts 82: 124 676};
J. Zhang et al., Guangzhou Huagong 20(3), 19–21 (1992) {see also Chemical Abstracts 121: 256 359};
N. Shindo et al., Meiji Daigaku Nogakubu Kenkyu Hokoku 74, 7–27 (1986) {see also Chemical Abstracts 108: 21 343}, can be obtained by a similar method.

Process C)

Substituted 2-phenylpyridines of the formula I where n is zero are oxidized in a manner known per se {cf., for example, A. Albini and S. Pietra, Heterocyclic N-Oxides, CRC-Press Inc., Boca Raton, U.S.A. 1991; H. S. Mosher et al., Org. Synth. Coll. Vol. IV 1963, page 828; E. C. Taylor et al., Org. Synth. Coll. Vol. IV 1963, page 704; T. W. Bell et al., Org. Synth. 69, 226 (1990)}:

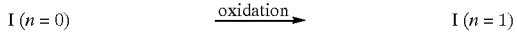

Amongst the oxidants conventionally used for oxidizing the pyridine ring, the following may be mentioned by way of example: peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Examples of suitable solvents are water, sulfuric acid, carboxylic acid, such as acetic acid and trifluoroacetic acid, and halogenated hydrocarbons, such as dichloromethane and chloroform.

The oxidation is usually successfully carried out at from 0° C. to the boiling point of the reaction mixture.

The oxidant is usually employed in at least equimolar amounts based on the starting compound. In general, however, a large excess of oxidant has proved to be particularly advantageous.

Unless otherwise specified, all the above-described processes are expediently carried out under atmospheric pressure or under the inherent pressure of the reaction mixture in question.

As a rule, the reaction mixtures are worked up in a manner known per se, for example by diluting the reaction mixture with water and subsequently isolating the product of value by means of filtration, crystallization or solvent extraction, or by removing the solvent, partitioning the residue in a mixture of water and a suitable organic solvent, and working up the organic phase to obtain the product.

In general, the substituted 2-phenylpyridines I can be prepared by one of the synthetic methods mentioned above. However, it may be more expedient for economical or process technology reasons to prepare some compounds I from similar substituted 2-phenylpyridines I which, however, differ in particular regarding the radial $R^7$.

The substituted 2-phenylpyridines of the formula I may contain one or more chiral centers, in which case they are usually obtained during the preparation as enantiomer or diastereomer mixtures. If desired, the mixtures can be separated into the essentially pure isomers by customary methods, for example by means of crystallization or chromatography on an optically active adsorbate. Pure optically active isomers may also be prepared, for example, from the corresponding optically active starting materials.

The compounds I, both as isomer mixtures and in the form of the pure isomers, are suitable as herbicides. The herbicidal compositions comprising I very effectively control vegetation in non-crop areas, especially at high rates of application. They act against broad-leaved weeds and grass weeds in crops such as wheat, rice, maize, soya and cotton without harming the crop plants to a substantial degree. This effect is mainly observed at low rates of application.

Depending on the application method in question, the compounds I, or the compositions comprising them, can also be employed in a further number of crop plants for removing undesirable plants. Suitable crops are, for example, those which follow:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

Moreover, the compounds I can also be used in crops which tolerate the action of herbicides as a result of breeding, including genetic engineering methods.

In addition, the substituted 2-phenylpyridines I are also suitable for the desiccation and/or defoliation of plants.

As desiccants, they are suitable, in particular, for the desiccation of the aerial parts of crop plants such as potatoes, oilseed rape, sunflowers and soya beans. This allows completely mechanical harvesting of these important crop plants.

Also of economic interest is facilitating harvesting, which is made possible by the dehiscence, or by reducing adherence to the tree, over a concentrated period of time, in citrus fruit, olives or in other species and varieties of pomaceous fruit, stone fruit and hard-shelled fruit. The same mechanism, i.e. promotion of the formation of abscission tissue between fruit or leaf and shoot of the plants is also essential for well-controlled defoliation of crop plants, in particular cotton.

Moreover, reducing the interval of time within which the individual cotton plants ripen improves the fiber quality post-harvest.

The compounds I or the compositions comprising them can be applied, for example, in the form of ready-to-spray aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Suitable inert additives are, essentially, mineral oil fractions of medium to high boiling point, such as kerosene or diesel oil, furthermore coal tar oils and oils of vegetable or animal origin, aliphatic, cyclic or aromatic hydrocarbons, for example paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, and which are suitable for dilution with water.

Suitable surfactants (adjuvants) are the alkali metal salts, alkaline earth metal salts and ammonium salts of aromatic sulfonic acids, e.g. lignosulfonic acid, phenolsulfonic acid, naphthalenesulfonic acid and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene-sulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignosulfite waste liquors or methylcellulose.

Powders, material for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powder, or other solid carriers.

The concentrations of the active ingredients I in the ready-to-use products can be varied within wide ranges. The formulations generally comprise from 0.001 to 98% by weight, preferably 0.01 to 95% by weight, of at least one active ingredient. The active ingredients I are employed in a purity from 90% to 100%, preferably 95% to 100% (in accordance with NMR spectrum).

The formulation examples which follow illustrate the preparation of such products:

I. 20 parts by weight of compound No. Ia.10 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of the calcium salt of dodecylbenzenesulfonic acid and 5 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

II. 20 parts by weight of compound No. Ia.19 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

III. 20 parts by weight of active ingredient No. Ia.32 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

IV. 20 parts by weight of active ingredient No. Ia.33 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of active ingredient No. Ia.34 are mixed with 97 parts by weight of finely divided kaolin. This gives a dust comprising 3% by weight of the active ingredient.

VI. 20 parts by weight of active ingredient No. Ia.43 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of active ingredient No. Ia.10 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of active ingredient No. Ia.19 is dissolved in a mixture composed of 80 parts by weight of cyclohexanone and 20 parts by weight of Wettol® EM 31 (=non-ionic emulsifier based on ethoxylated castor oil). This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the naked soil surface (post-directed, lay by).

The application rates of active ingredient I are from 0.001 to 3.0, preferably 0.01 to 1.0, kg/ha active ingredient (a.i.), depending on the control target, the season, the target plants and the growth stage.

To widen the spectrum of action and to achieve synergistic effects, the substituted 2-phenylpyridines I may be mixed with a large number of representatives of other groups of herbicidal or growth-regulating active ingredients and then applied concomitantly. Examples of suitable components for mixtures are 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to apply the compounds I, alone or in combination with other herbicides, together with further crop protection agents, for example with pesticides or agents for controlling phytopathogenic fungi or bacteria. Also of interest is the miscibility with mineral salt solutions which are employed for treating nutrient and trace element deficiencies. Non-phytotoxic oils and oil concentrates may also be added.

PREPARATION EXAMPLES

Example 1 (Compound No. Ia.10 in Table 1)

The compound was prepared in accordance with the following equation:

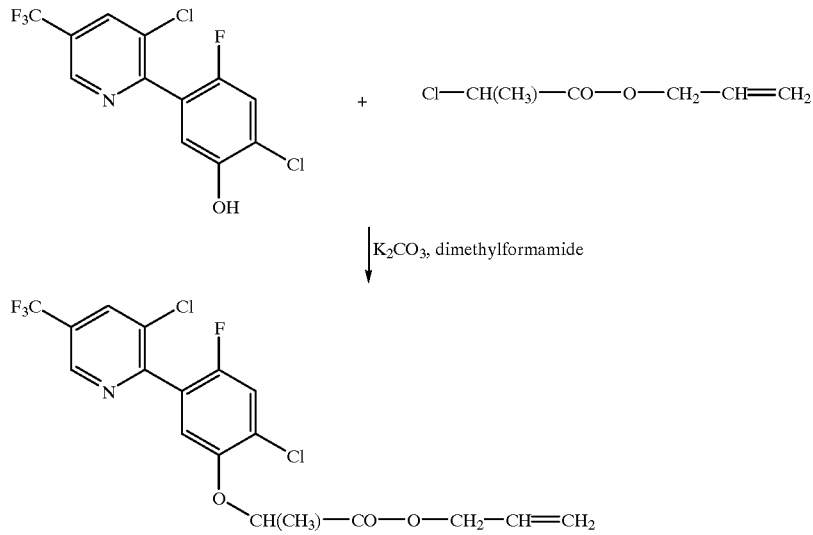

1.5 g of 3-chloro-2-(4-chloro-2-fluoro-5-hydroxyphenyl)-5-trifluoromethylpyridine, 1.5 g of allyl 2-chloropropionate and 1.4 g of potassium carbonate were stirred for 4 hours at 80° C. in 50 ml of anhydrous dimethylformamide under a nitrogen atmosphere. After cooling, the reaction mixture was poured into 200 ml of ice-water. The product was subsequently extracted using three times 100 ml of methyl tert-butyl ether. The combined organic phases were washed twice using 50 ml of water in each case and then dried over sodium sulfate and concentrated. The crude product was purified by chromatography on silica gel (eluent: cyclohexane/methyl tert-butyl ether=9:1). Yield: 1.7 g of a colorless oil of a purity of approximately 99% (according to HPLC analysis).

$^1$H NMR (250 MHz; in CDCl$_3$): δ[ppm]=1.71 (d,3H); 4.65 (d,2H); 4.80 (q,1H); 5.17–5.35 (m,2H); 5.78–5.95 (m,1H); 7.01 (d,1H); 7.28 (d,1H); 8.05 (s,1H); 8.84 (s,1H).

Example 2 (Compound No. Ia.19 in Table 1)

The compound was prepared in accordance with the following equation:

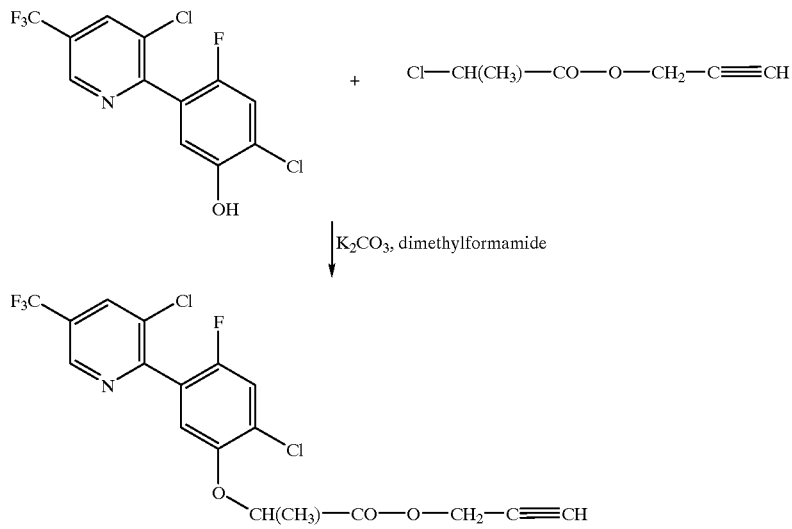

The reaction was carried out by a method similar to Example 1 using 1.5 g of 3-chloro-2-(4-chloro-2-fluoro-5-hydroxyphenyl)-5-trifluoromethyl-pyridine, 1.5 g of propargyl 2-chloropropionate and 1.4 g of potassium carbonate. Yield: 0.7 g of a colorless oil.

$^1$H NMR (250 MHz; in CDCl$_3$): δ[ppm]1.71 (d,3H); 2.41 (t,1H); 4.74 (d,2H); 4.80 (q,1H); 7.03 (d,1H); 7.28 (d,1H); 8.06 (s,1H); 8.85 (s,1H).

Example 3 (Compound No. Ia.32 in Table 1)

The compound was prepared in accordance with the following equation:

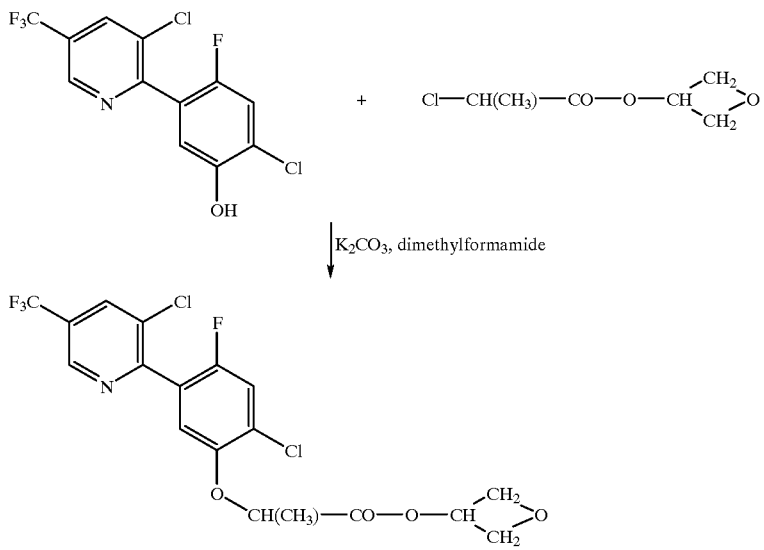

The reaction was carried out by a method similar to Example 1 using 1.5 g of 3-chloro-2-(4-chloro-2-fluoro-5-hydroxyphenyl)-5-trifluoromethylpyridine, 1.7 g of 3-oxetanyl 2-chloropropionate and 1.4 g of potassium carbonate. Yield: 1.3 g of a colorless oil.

$^1$H NMR (250 MHz; in CDCl$_3$): δ[ppm]=1.73 (d,3H); 4.55–4.69 (m,2H); 4.77–4.93 (m,3H); 5.50 (p,1H); 7.03 (d,1H); 7.30 (d,1H); 8.06 (s,1H); 8.85 (s,1H).

The 3-oxetanyl 2-chloropropionate used was prepared in accordance with the following equation:

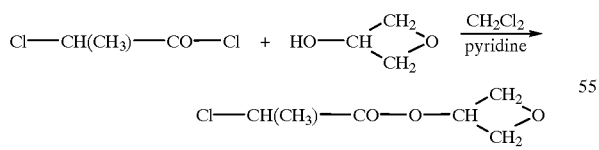

8.6 g of 2-chloropropionyl chloride were added dropwise at 0 to 5° C. to a mixture of 5.0 g of 3-hydroxyoxetane, 5.9 g of anhydrous pyridine and 50 ml of anhydrous dichloromethane, whereupon the mixture was stirred for 48 hours at 23° C. Then, the reaction mixture was washed three times using 50 ml of water in each case and subsequently dried over sodium sulfate and finally concentrated. The crude product was purified by distillation at a pressure of 0.3 mbar (b.p.: 90° C.).

$^1$H NMR (250 MHz; in CDCl$_3$): δ[ppm]=1.70 (d,3H); 4.46 (q,1H); 4.67 (t,2H); 4.90 (t,2H); 5.50 (p,1H).

Example 4 (Compound No. Ia.33 in Table 1)

The compound was prepared in accordance with the following equation:

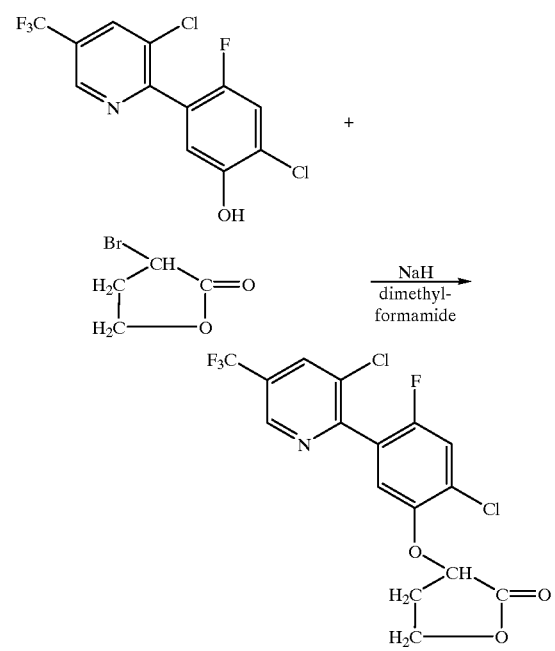

0.2 g of an 80% by weight suspension of sodium hydride in mineral oil was freed from the mineral oil by suspending in dimethylformamide and decanting. The residue was suspended in 50 ml of anhydrous dimethylformamide. Then, a solution of 2.0 g of 3-chloro-2-(4-chloro-2-fluoro-5-hydroxyphenyl)-5-trifluoromethylpyridine in 10 ml of dimethylformamide was added dropwise at 0 to 5° C., whereupon the mixture was stirred for 15 minutes. 2.2 g of α-bromo-γ-butyrolactone were subsequently added dropwise to the mixture. The mixture was then stirred for six hours at 80° C. After cooling, the reaction mixture was poured into 200 ml of ice-water. The product was extracted three times using 100 ml of ethyl tert-butyl ether, whereupon the combined organic phases ere washed twice using 100 ml of water in each case, then dried over sodium sulfate and subsequently concentrated. Yield: 2.2 g of a colorless oil.

$^1$H NMR (270 MHz; in CDCl$_3$): δ[ppm]=2.53–2.81 (m,2H); 4.34 (q,1H); 4.50–4.60 (m,1H); 4.92 (t,1H); 7.28 (d,1H); 7.40 (d,1H); 8.07 (s,1H); 8.83 (s,1H).

Example 5 (Compound No. Ia.34 in Table 1)

The compound was prepared in accordance with the following equation:

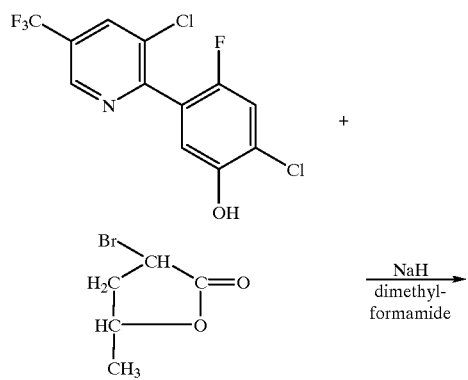

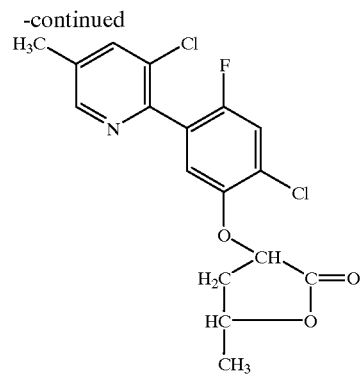

The reaction was carried out by a method similar to Example 4 using 2.0 g of 3-chloro-2-(4-chloro-2-fluoro-5-hydroxyphenyl)-5-trifluoromethylpyridine and 1.2 g of 2-bromo-4-methyl-γ-butyrolactone. Yield: 2.4 g of a colorless oil (diastereomer mixture).

$^1$H NMR (270 MHz; in CDCl$_3$): δ[ppm]=1.47 (d,3H; MD$^{1)}$); 1.54 (d,3H; MD$^{2)}$), 2.15–2.30 (m,1H; MD+SD); 2.65–2.75 (m,1H; SD); 2.83–2.97 (m,1H; MD); 4.53–4.66 (m,1H; MD); 4.86–4.98 (m,1H; SD); 4.99 (t,1H; MD+SD); 7.27 (d,1H; MD+SD); 7.40 (d,1H; MD); 7.44 (d,1H; SD); 8.06 (s,1H; MD+SD); 8.83 (s,1H; MD+SD).

1) Secondary diastereomer
2) Main diastereomer

Example 6 (Compound No. Ia.43 in Table 1)

The compound was prepared in accordance with the following equation:

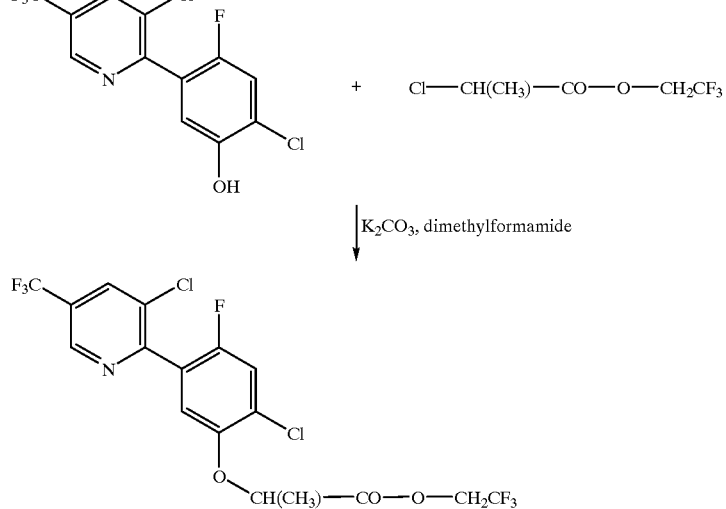

The reaction was carried out by a method similar to Example 1 using 1.5 g of 3-chloro-2-(4-chloro-2-fluoro-5-hydroxyphenyl)-5-trifluoromethyl-pyridine and 1.9 g of 2',2',2'-trifluoroethyl 2-chloropropionate. Yield: 0.4 g of a colorless oil.

$^1$H NMR (250 MHz; in CDCl$_3$): δ[ppm]=1.74 (d,3H); 4.43–4.63 (m,2H); 4.87 (q,1H); 7.01 (d,1H); 7.29 (d,1H); 8.04 (s,1H); 8.83 (s,1H).

Use Examples (herbicidal activity)

The herbicidal action of the substituted 2-phenylpyridines I was demonstrated by the following greenhouse experiments:

The culture containers used were plastic flowerpots containing loamy sand with approximately 3.0% of humus as the substrate. The seeds of the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover resulted in uniform germination of the test plants, unless germination was adversely affected by the active ingredients.

For the post-emergence treatment, the test plants were first grown to a plant height of 3 to 15 cm, depending on the plant habit, and only then treated with the active ingredients which were suspended or emulsified in water. The test plants were either sown directly and grown in the same containers, or first grown separately as seedlings and then transplanted to the test containers a few days prior to treatment. The application rate for the post-emergence treatment was 0.0039 or 0.0019 kg/ha of a.i. (active ingredient).

Depending on the species, the plants were kept at from 10 to 25° C. or 20 to 35° C. The test period extended to 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

The plants used in the greenhouse experiments belonged to the following species:

| Scientific Name | Common Name |
| --- | --- |
| Zea mays | Indian corn |
| Abutilon theophrasti | velvet leaf |
| Chenopodium album | lambsquarters (goosefoot) |
| Ipomoea subspecies | morningglory |
| Solanum nigrum | black nightshade |

Applied post-emergence at an application rate of 0.0039 or 0.0019 kg/ha of a.i., compound No. Ia.43 showed a very good and selective action against the abovementioned weeds and good tolerance by the crop plant Indian corn.

The comparison compound known from WO 95/02580 (No. I.514)

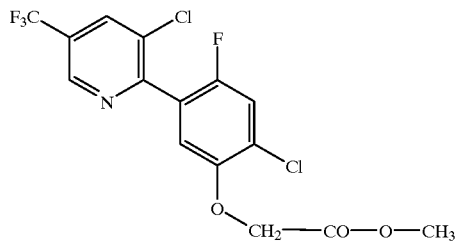

in contrast, damaged not only the undesirable plants, but also the Indian corn to an unacceptably high degree.

Use Examples (desiccant/defoliant activity)

The test plants used were young cotton plants with 4 leaves (without cotyledons), which were grown under greenhouse conditions (relative atmospheric humidity 50 to 70%; day/night temperature 27/20° C.).

The young cotton plants were subjected to foliar treatment to runoff point using aqueous preparations of the active ingredients (with an addition of 0.15% by weight of the fatty alcohol alkoxylate Plurafac® LF 700[1], based on the spray mixture). The amount of water applied was 1000 l/ha (converted). After 13 days, the number of shed leaves and the degree of defoliation in % were determined.

[1] a low-foam nonionic surfactant from BASF AG

No leaves were shed amongst the untreated control plants.

We claim:

1. A substituted 2-phenylpyridine of the formula I

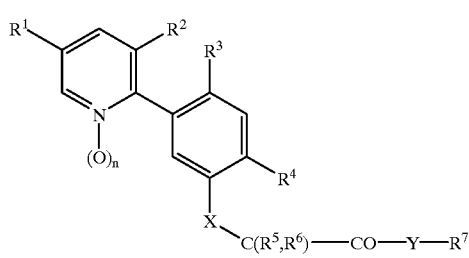

where the variables have the following meanings:

n is 0 or 1;

$R^1$ is halogen or $C_1$–$C_6$-haloalkyl;

$R^2$ and $R^3$ independently of one another are hydrogen or halogen;

$R^4$ is cyano or halogen;

X and Y independently of one another are oxygen or sulfur;

$R^5$ and $R^6$ independently of one another are hydrogen or $C_1$–$C_4$-alkyl or together are a 1,2-ethylene, 1,3-propylene, 1,4-tetramethylene or 1,5-pentamethylene chain;

$R^7$ is $C_1$–$C_6$-haloalkyl, $C_3$–$C_6$-haloalkenyl, $C_2$–$C_6$-alkenyloxy-$C_1$–$C_4$-alkyl, $C_2$–$C_6$-alkenyloxy-$C_1$–$C_4$-alkoxy-$C_1$–$C_4$-alkyl, $C_3$–$C_6$-alkenyl, $C_3$–$C_6$-alkadienyl, $C_3$–$C_6$-alkynyl, $C_3$–$C_6$-cycloalkyl, $C_5$–$C_6$-cycloalkenyl, or $R^6$ and $R^7$ together are a 1,2-ethylene or 1,3-propylene chain which, if desired, can additionally have attached to it one or two $C_1$–$C_4$-alkyl substituents.

2. A substituted 2-phenylpyridine of the formula I as claimed in claim 1, where n is 0, $R^1$ is trifluoromethyl, $R^2$ is chlorine, $R^3$ is hydrogen or fluorine, $R^4$ is cyano or chlorine, X and Y are oxygen, $R^5$ and $R^6$ independently of one another are hydrogen or methyl and $R^7$ is $C_1$–$C_6$-haloalkyl, $C_3$–$C_6$-alkenyl, $C_3$–$C_6$-alkynyl, $C_3$–$C_6$-cycloalkyl, or $R^6$ and $R^7$ together are a 1,2-ethylene or 1,3-propylene chain.

3. A herbicidal composition comprising a herbicidally active amount of at least one substituted 2-phenylpyridine of the formula I as claimed in claim 1 and at least one inert liquid and/or solid carrier and, if desired, at least one surfactant.

4. A composition for the desiccation and/or defoliation of plants comprising such an amount of at least one substituted/2-phenylpyridine of the formula I as claimed in claim 1 that it acts as a desiccant and/or defoliant, and at least one inert liquid and/or solid carrier and, if desired, at least one surfactant.

5. A process for the preparation of herbicidally active compositions which comprises mixing a herbicidally active amount of at least one substituted 2-phenylpyridine of the formula I as claimed in claim 1 and at least one inert liquid and/or solid carrier and, if desired, at least one surfactant.

6. A process for the preparation of compositions which act as desiccants and/or defoliants, which comprises mixing such an amount of at least one substituted 2-phenylpyridine of the formula I as claimed in claim 1 that it acts as a desiccant and/or defoliant, and at least one inert liquid and/or solid carrier and, if desired, at least one surfactant.

7. A method of controlling undesirable vegetation, which comprises allowing a herbicidally active amount of at least one substituted 2-phenylpyridine of the formula I as claimed in claim 1 to act on plants, their environment or on seed.

8. A method for the desiccation and/or defoliation of plants, which comprises allowing such an amount of at least one substituted 2-phenylpyridine of the formula I as claimed in claim 1 to act on plants that it acts as a desiccant and/or defoliant.

9. A method as claimed in claim 8, wherein cotton is treated.

10. A process for the preparation of substituted 2-phenylpyridines of the formula I as claimed in claim 1, which comprises reacting a 3-pyridyl(thio)phenol of the formula III

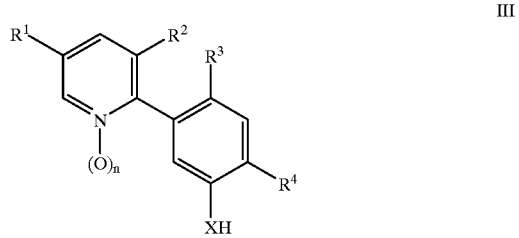

or a salt of III in a manner known per se with an alkylating agent of the formula IV $$L\text{—}C(R^5,R^6)\text{—}CO\text{—}Y\text{—}R^7 \qquad \text{IV}$$

where L is chlorine, bromine, iodine, methylsulfonyloxy, trifluoromethylsulfonyloxy, phenylsulfonyloxy or p-toluenesulfonyloxy
in an inert solvent or diluent in the.presence or absence of a base.

* * * * *